US010151808B2

(12) United States Patent
Xiao et al.

(10) Patent No.: US 10,151,808 B2
(45) Date of Patent: Dec. 11, 2018

(54) MULTI-DETECTING DEPTH NUCLEAR MAGNETIC RESONANCE LOGGING TOOL AND PROBE, AND ANTENNA EXCITATION METHOD

(71) Applicant: CHINA UNIVERSITY OF PETROLEUM-BEIJING, Beijing (CN)

(72) Inventors: Lizhi Xiao, Beijing (CN); Zhe Sun, Beijing (CN); Guangzhi Liao, Beijing (CN); Sihui Luo, Beijing (CN); Xin Li, Beijing (CN); Qunjie Du, Beijing (CN); Wei Liu, Beijing (CN); Weiliang Chen, Beijing (CN); Jie Wang, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 189 days.

(21) Appl. No.: 15/258,731

(22) Filed: Sep. 7, 2016

(65) Prior Publication Data
US 2017/0085008 A1 Mar. 23, 2017

(30) Foreign Application Priority Data

Sep. 23, 2015 (CN) .......................... 2015 1 0614228

(51) Int. Cl.
*H01Q 1/38* (2006.01)
*G01R 33/3415* (2006.01)
*G01N 24/08* (2006.01)

(52) U.S. Cl.
CPC ....... *G01R 33/3415* (2013.01); *G01N 24/081* (2013.01)

(58) Field of Classification Search
CPC ........ H01Q 1/38; H01Q 7/08; G01R 33/3415; G01N 24/081
(Continued)

(56) References Cited

U.S. PATENT DOCUMENTS 6,249,259 B1 * 6/2001 Goodman ................ H01Q 7/08
340/854.6
2003/0210050 A1 11/2003 Prammer et al. ............. 324/315
(Continued)

FOREIGN PATENT DOCUMENTS

CN 101098047 A 1/2008
CN 102519999 A 6/2012
(Continued)

OTHER PUBLICATIONS

The Chinese First Examination Report of corresponding China patent application No. 201510614228.4, dated Aug. 16, 2017.

*Primary Examiner* — Huedung Mancuso
(74) *Attorney, Agent, or Firm* — J.C. Patents

(57) ABSTRACT

The present invention provides a multi-detecting depth nuclear magnetic resonance logging tool and probe, and an antenna excitation method, the probe of nuclear magnetic resonance logging tool includes: a housing, a magnet and an antenna array apparatus; the magnet is fixedly arranged in the housing; the antenna array apparatus includes at least two groups of antenna arrays distributed along circumference of the magnet, and each group of antenna arrays include N layers of independently fed antennas; k-th layer antenna is arranged between the magnet and (k+1)-th layer antenna, k=1, 2, . . . N−1; the antenna is fixed on a support, and the support is fixedly connected to the housing. In the present invention, stratum information detection at different azimuth angles is achieved by exciting different antenna arrays, so that circumferential recognizing capability of nuclear magnetic resonance logging tool probe is improved (Continued)

and three-dimensional (radial, axial and circumferential) stratum detection is achieved.

9 Claims, 2 Drawing Sheets

(58) Field of Classification Search
USPC .................................. 343/700 MS, 787, 788
See application file for complete search history.

(56) References Cited

U.S. PATENT DOCUMENTS

| | | | |
|---|---|---|---|
| 2007/0061082 A1* | 3/2007 | Seleznev | G01V 3/26 |
| | | | 702/11 |
| 2008/0174309 A1 | 7/2008 | Pusiol et al. | 324/306 |
| 2009/0121711 A1* | 5/2009 | Blanz | G01N 24/081 |
| | | | 324/303 |
| 2009/0167302 A1* | 7/2009 | Edwards | G01V 3/32 |
| | | | 324/303 |
| 2013/0127463 A1* | 5/2013 | Matschl | G01R 33/34 |
| | | | 324/309 |
| 2016/0238734 A1* | 8/2016 | Valori | E21B 47/0905 |

FOREIGN PATENT DOCUMENTS

| | | |
|---|---|---|
| CN | 203594440 U | 5/2014 |
| CN | 203867568 U | 10/2014 |

\* cited by examiner

MULTI-DETECTING DEPTH NUCLEAR MAGNETIC RESONANCE LOGGING TOOL AND PROBE, AND ANTENNA EXCITATION METHOD

CROSS-REFERENCE TO RELATED APPLICATIONS

This application claims priority to Chinese Patent Application No. 201510614228.4, filed on Sep. 23, 2015, the content of which is hereby incorporated by reference in its entirety.

TECHNICAL FIELD

The present invention relates to the technical field of nuclear magnetic resonance logging, and more particularly to a probe of nuclear magnetic resonance logging tool, a nuclear magnetic resonance logging tool and an antenna excitation method.

BACKGROUND

The phenomenon of nuclear magnetic resonance (Nuclear Magnetic Resonance, NMR) is applied in fields, such as physics, chemistry, material science, life science and medical science, shortly after being found in 1946. In 1950s, the nuclear magnetic resonance came into use in the oil and gas industry, and originally applied to the field of oil reservoir rock physics. A nuclear magnetic resonance logging tool can utilize the nuclear magnetic resonance principle to detect stratum information around the borehole, and have unique capabilities of qualitative recognition and quantitative evaluation for the reservoir fluid.

A probe is one of the important parts in the nuclear magnetic resonance logging tool, and the structure of the probe determines key performances, such as a measuring mode of the tool, a nuclear magnetic resonance region and nuclear magnetic resonance signal intensity. The probe of nuclear magnetic resonance logging tool mainly includes a magnet and an antenna, the magnet can form a static magnetic field for polarizing spinning hydrogen protons, and the antenna can emit a radio frequency field for turning the spinning hydrogen protons, after the radio frequency field is removed, the spinning hydrogen protons start to precess along the static magnetic field, thus generate nuclear magnetic resonance inductive signals, and the stratum conditions can be analyzed by detecting the nuclear magnetic resonance inductive signals.

The existing probe of nuclear magnetic resonance logging tool usually adopts a column-shaped magnet, rounded sides of the magnet are an N pole and an S pole, respectively, the magnetic field distribution is formed by closed magnetic lines of force pointing from the N pole to the S pole, the antenna surrounds the magnet, and can excite polarized stratum regions all around (360 degrees) the borehole, so that there is no detecting blind zone around the borehole, a multi-frequency multi-slice measurement can be performed, but the measuring signal is only an average signal of signals in the 360-degree stratum. Accordingly, the probe of nuclear magnetic resonance logging tool in the prior art only can perform signal detection at radial depth dimension and axial depth dimension, but have no capability to detect signals in the circumferential multi-azimuth sensitive area.

SUMMARY

The present invention provides a probe of a nuclear magnetic resonance logging tool, a nuclear magnetic resonance logging tool and an antenna excitation method, so as to solve the technical problems that the nuclear magnetic resonance logging tool probe in the prior art only can perform signal detection at radial depth dimension and axial depth dimension, but have no capability to detect signals in the circumferential multi-azimuth sensitive area.

The present invention provides a probe of a nuclear magnetic resonance logging tool, including: a housing, a magnet and an antenna array apparatus;

The magnet is fixedly arranged in the housing;

The antenna array apparatus includes at least two groups of antenna arrays distributed along a circumference of the magnet, and each group of the antenna arrays include N layers of independently fed antennas;

A k-th layer antenna is arranged between the magnet and a (k+1)-th layer antenna, k=1, 2, . . . N−1;

The antenna is fixed on a support, and the support is fixedly connected to the housing.

Furthermore, the antenna array apparatus includes at least one group of reflective antenna arrays, a first layer antenna of the reflective antenna array is a reflective antenna, and a second layer antenna is a saddle-type antenna or a strip-type antenna;

The reflective antenna has a greater surface area than the strip-type antenna.

Furthermore, the reflective antenna and the strip-type antenna are arc-shaped, a center of the reflective antenna is recessed away from the magnet, and a center of the strip-type antenna is recessed towards the magnet.

Furthermore, the strip-type antenna has a less arc curvature than the reflective antenna.

Furthermore, the nuclear magnetic resonance logging tool probe also includes: an antenna excitation circuit for feeding the antenna;

Multiple layers of antennas in the antenna array are electrically connected to the antenna excitation circuit respectively.

Furthermore, the magnet is a cylindrical magnet, the cylindrical magnet is magnetized radially, and the antenna array apparatus includes multi groups of antenna arrays uniformly distributed along a circumference of the magnet.

Furthermore, when the nuclear magnetic resonance logging tool is used as a partial tool, the magnet includes a main magnet and a shielding magnet, both the main magnet and the shielding magnet are of a cuboid shape, and the main magnet has a larger thickness than the shielding magnet;

There are at least two groups of antenna arrays arranged at one side of the main magnet when the nuclear magnetic resonance logging tool is used as a partial tool.

Furthermore, the magnet has a cyclic structure, a mud pipe through which drilling fluid is circulated is penetrated through the housing, and the magnet is sleeved on the mud pipe;

The at least two groups of antenna arrays are uniformly distributed along a circumference of the magnet.

The present invention also provides a nuclear magnetic resonance logging tool including any of the nuclear magnetic resonance logging tool probes described above.

The present invention also provides an antenna excitation method based on any of the nuclear magnetic resonance logging tool probes described above.

Exciting antennas in one group of antenna arrays, to achieve a mono-azimuth angle detection;

Exciting antennas in at least two groups of antenna arrays, to achieve a multi-azimuth angle detection;

Exciting antennas in different layers of the same antenna array, to achieve detection at different radial depths.

In the probe of the nuclear magnetic resonance logging tool, the nuclear magnetic resonance logging tool and the antenna excitation method provided in the present invention, at least two groups of antenna arrays are distributed along a circumference of the magnet, and each group of the antenna arrays include at least two layers of independently fed antennas, stratum information detection at different azimuth angles can be achieved by exciting different antenna arrays, so that circumferential recognizing capability of the nuclear magnetic resonance logging tool probe can be improved and three-dimensional (radial, axial and circumferential) stratum detection can be achieved; besides, the first layer antenna is arranged between the magnet and the second layer antenna, stratum information detection at different radial depths can be achieved by exciting different layer antennas, and detecting capability at radial depths can be further improved.

DESCRIPTION OF REFERENCE SIGNS

1—magnet; 2—antenna array apparatus; 21—first layer antenna; 22—second layer antenna.

DESCRIPTION OF EMBODIMENTS

In order to make the objects, technical solutions, and advantages of the embodiments of the present invention clearer, the technical solutions in the embodiments of the present invention are hereinafter described clearly and completely with reference to the accompanying drawings in the embodiments of the present invention. Obviously, the embodiments described here are part of the embodiments of the present invention and not all of the embodiments. All other embodiments obtained by persons skilled in the art on the basis of the embodiments of the present invention without any creative efforts all fall within the scope of the invention.

Embodiment 1

Figure 1:
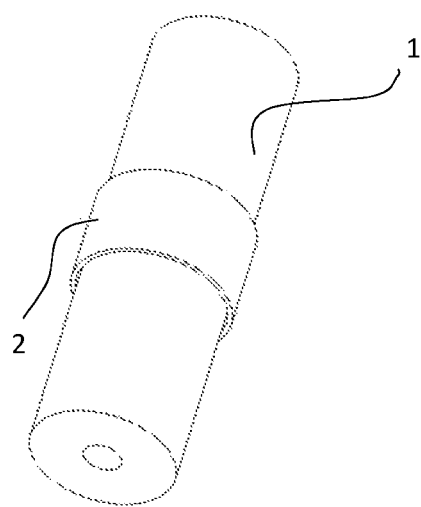
FIG. 1 is a structural schematic diagram of a probe of a nuclear magnetic resonance logging tool according to Embodiment 1 of the present invention.

Embodiment 1 of the present invention provides a probe of a nuclear magnetic resonance logging tool. FIG. 1 is a structural schematic diagram of a probe of a nuclear magnetic resonance logging tool according to Embodiment 1 of the present invention. As shown in FIG. 1, the probe of the nuclear magnetic resonance logging tool in this embodiment includes a housing (not shown), a magnet 1 and an antenna array apparatus 2;

The magnet 1 is fixedly arranged in the housing;

The antenna array apparatus 2 includes at least two groups of antenna arrays distributed along a circumference of the magnet 1, and each group of the antenna arrays include N-layer independently fed antennas;

The k-th layer antenna is arranged between the magnet 1 and the (k+1)-th layer antenna, N is a natural number great than or equal to 2, and k=1, 2, . . . N−1;

The antenna is fixed on a support, and the support is fixedly connected to the housing.

In particular, the magnet 1 can be of cylindrical, cuboid, annular or irregular shape, the antenna array apparatus 2 includes multiple groups of antenna arrays, which are radio frequency antenna arrays, the multiple groups of antenna arrays, which may have the same or different types, are distributed along the circumference of the magnet 1.

Figure 2:
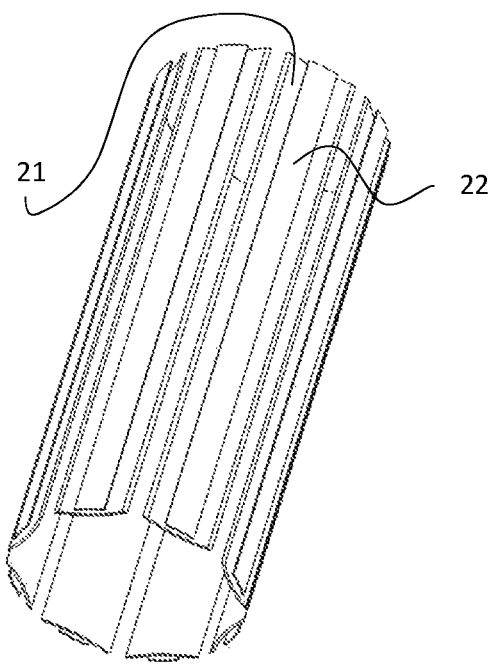
FIG. 2 is a structural schematic diagram of an antenna array apparatus in a probe of a nuclear magnetic resonance logging tool according to Embodiment 2 of the present invention.
Figure 3:
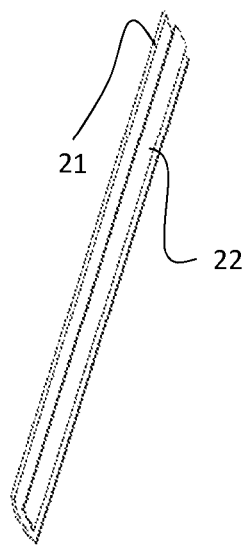
FIG. 3 is a structural schematic diagram of an antenna array in a probe of a nuclear magnetic resonance logging tool according to Embodiment 3 of the present invention.

Each group of antenna arrays can include multi-layer of antennas, where, the first layer antenna is arranged outside the magnet 1, the second layer antenna is arranged outside the first layer antenna, by such analogy, the (k+1)-th layer antenna is arranged outside the k-th layer antenna, that is, multiple antennas are arranged in layers outside the magnet 1. FIG. 2 is a structural schematic diagram of an antenna array apparatus in a probe of a nuclear magnetic resonance logging tool according to Embodiment 2 of the present invention, and FIG. 3 is a structural schematic diagram of an antenna array in a probe of a nuclear magnetic resonance logging tool according to Embodiment 3 of the present invention. As shown in FIG. 2 and FIG. 3, the antenna array apparatus 2 includes multiple groups of antenna arrays, the antenna array includes two layers of antennas, and the first layer antenna 21 is arranged between the magnet 1 and the second layer antenna 22.

The antenna can be fixed to the housing via a support, each antenna is independently fed, particularly, the probe of the nuclear magnetic resonance logging tool in this embodiment also can include: an antenna excitation circuit for feeding the antenna; the antenna excitation circuit can include multiple excitation channels, and multiple antennas can be connected to different excitation channels, respectively. When different antennas are excited, stratum information at different areas can be detected, the manner for exciting an antenna belongs to the prior art, and therefore no more details are given in this embodiment.

In practical work, the magnet 1 generates a static magnetic field and the antenna generates a radio frequency field, the two fields jointly act on stratum around the borehole, and thus stratum information detection can be achieved. In the probe provided in this embodiment, multiple antenna arrays are distributed around the magnet 1, a mono-azimuth angle stratum information detection can be achieved by separately exciting a single antenna array, and stratum information detection at different azimuth angles can be achieved by simultaneously exciting multiple antenna arrays; in one group of antenna arrays, stratum information detection at a nearer region can be achieved by separately exciting a single antenna, and stratum information detection at a farther region can be achieved by simultaneously exciting multiple antennas. It is assumed that the probe is provided with two groups of antenna arrays A and B, A and B are distributed at the left and right sides of the magnet 1 respectively, antenna array A is provided with two layers of antennas A1 and A2, antenna array B is provided with two layers of antennas B1 and B2, then detection results obtained by exciting different antennas are shown in Table 1.

TABLE 1

| Mode | A1 | A2 | B1 | B2 | Result |
|---|---|---|---|---|---|
| 1 | + | + | + | + | Stratum information at a farther region on both left and right sides can be detected |
| 2 | + | + | + | − | Stratum information at a farther region on the left side, at a nearer region on the right side can be detected |
| 3 | + | + | − | + | Stratum information at a farther region on the left side, at a nearer region on the right side can be detected |
| 4 | + | + | − | − | Stratum information at a farther region on the left side can be detected |
| 5 | + | − | + | + | Stratum information at a nearer region on the left side, at a farther region on the right side can be detected |
| 6 | + | − | + | − | Stratum information at a nearer region on the left side, at a nearer region on the right side can be detected |
| 7 | + | − | − | + | Stratum information at a nearer region on the left side, at a nearer region on the right side can be detected |
| 8 | + | − | − | − | Stratum information at a nearer region on the left side can be detected |
| 9 | − | + | + | + | Stratum information at a nearer region on the left side, at a farther region on the right side can be detected |
| 10 | − | + | + | − | Stratum information at a nearer region on the left side, at a nearer region on the right side can be detected |
| 11 | − | + | − | + | Stratum information at a nearer region on the left side, at a nearer region on the right side can be detected |
| 12 | − | + | − | − | Stratum information at a nearer region on the left side can be detected |
| 13 | − | − | + | + | Stratum information at a farther region on the right side can be detected |
| 14 | − | − | + | − | Stratum information at a nearer region on the right side can be detected |
| 15 | − | − | − | + | Stratum information at a nearer region on the right side can be detected |
| 16 | − | − | − | − | None |

In Table 1, + indicates that the antenna is in an excited state, − indicates that the antenna is in a non-excited state, when antenna array A and antenna array B are excited simultaneously, stratum information on both left and right sides can be detected, then the information detected by the antenna is an average value of nuclear magnetic resonance signals in regions on both left and right sides, when only one group of antennas are excited, nuclear magnetic resonance signals in regions on one side can be detected, besides, stratum information on the other side can be deduced based on the signal average value on both sides when excited simultaneously as well as signals at one side when excited separately. When the antenna array is excited, if the two layers of antennas has different structures and excitation manners, then stratum information at different radial depths can be detected by separately exciting different antennas, such as mode 14 and mode 15 in Table 1, although the stratum information at a nearer region on the right side is detected, the two modes may correspond to different radial depths.

When the number of antenna arrays in the antenna array apparatus 2 is more than 2, or the number of the antenna layers in the antenna arrays is more than 2, then more detection results can be obtained, for example, the antenna array apparatus shown in FIG. 2 includes 8 groups of antenna arrays, each group of antenna arrays include two layers of antennas, then there can be 16×16=256 different detection modes, the circumferential recognizing capability can be higher.

In the probe of nuclear magnetic resonance logging tool provided in the this embodiment, at least two groups of antenna arrays are distributed along the circumference of the magnet 1, and each group of the antenna arrays include at least two layers of independently fed antennas, stratum information detection at different azimuth angles can be achieved by exciting different antenna arrays, so that circumferential recognizing capability of The probe of the nuclear magnetic resonance logging tool can be improved and three-dimensional (radial, axial and circumferential) stratum detection can be achieved; besides, antennas are arranged in layers outside the magnet 1, stratum information detection at different radial depths can be achieved by exciting different antennas, and detecting capability at radial depths can be further improved.

On the basis of the technical solutions in the above embodiments, it is preferable that the antenna array apparatus 2 includes at least one group of reflective antenna arrays, a first layer antenna 21 of the reflective antenna array is a reflective antenna, and a second layer antenna 22 in the reflective antenna array can be a saddle-type antenna or a strip-type antenna or other types of antennas. The saddle-type antenna and the strip-type antenna are primarily intended for radiation, while the reflective antenna is primarily intended for focusing.

In the antenna array shown in FIG. 3, the first layer antenna 21 is a reflective antenna, and the second layer antenna 22 is a strip-type antenna, both the reflective antenna and the strip-type antenna are arc-shaped, the difference lies in that, a center of the reflective antenna is recessed towards the magnet 1, and a center of the strip-type antenna is recessed away from the magnet 1, that is, the center corresponding to arc of the reflective antenna and the magnet 1 are located at both sides of the reflective antenna, respectively while the center corresponding to arc of the strip-type antenna and the magnet 1 are located at the same side of the strip-type antenna.

Figure 4:
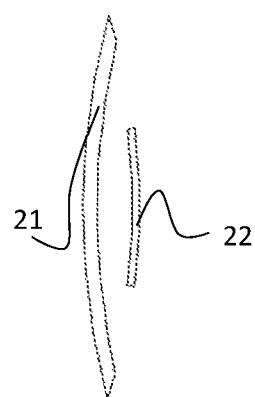
FIG. 4 is a side view of the antenna array in FIG. 3.

FIG. 4 is a side view of the antenna array in FIG. 3, as shown in FIG. 3 and FIG. 4, the reflective antenna has a greater surface area than the strip-type antenna, and the strip-type antenna has a less arc curvature than the reflective antenna. The strip-type antenna should be located outside the reflective antenna, only in this way, the reflective antenna can play a focusing role, to centralize signals generated by the strip-type antenna to farther stratum, and improve a radial detecting depth of the probe of the nuclear magnetic resonance logging tool.

Embodiment 2

Embodiment 2 of the present invention provides a probe of a nuclear magnetic resonance logging tool for use in a centered nuclear magnetic resonance logging tool. In the probe of the nuclear magnetic resonance logging tool provided in this embodiment, the magnet is a cylindrical magnet, the cylindrical magnet is magnetized radially, and the antenna array apparatus includes four groups of antenna arrays uniformly distributed along a circumference of the magnet; each group of the antenna arrays include at least two layers of independently fed antennas, and the first layer antenna is arranged between the magnet and the second layer antenna.

In the probe of the nuclear magnetic resonance logging tool provided in this embodiment, four groups of antenna arrays are uniformly distributed along the circumference of the magnet; stratum information detection at four different azimuth angles can be achieved by exciting different antenna arrays, so that circumferential recognizing capability of the probe of the nuclear magnetic resonance logging tool can be improved, and the centered nuclear magnetic resonance logging tool can be optimized.

Embodiment 3

Embodiment 3 of the present invention provides a probe of a nuclear magnetic resonance logging tool for use in a sidewall nuclear magnetic resonance logging tool. In the probe of the nuclear magnetic resonance logging tool provided in this embodiment, the magnet includes a main magnet and a shielding magnet, both the main magnet and the shielding magnet are of a cuboid shape, and the main magnet has a larger thickness than the shielding magnet; at least two groups of antenna arrays are arranged at one side of the main magnet; each group of the antenna arrays include at least two layers of independently fed antennas, and the first layer antenna is arranged between the magnet and the second layer antenna.

Particularly, magnetization directions of the main magnet and the shielding magnet are both perpendicular to the axial directions thereof, the shielding magnet can make the magnetic lines of force at a farther region more centralized, so that the static magnetic field generated by the main magnet can match orthogonally with the radio frequency field generated by the antenna over a larger range of angles. Besides, the probe also can be provided with a magnetic core, the antenna can be wound on the magnetic core, and the magnetic core can enhance the efficiency of the antenna.

In the probe of the nuclear magnetic resonance logging tool provided in this embodiment, at least two groups of antenna arrays are distributed at one side of the magnet; stratum information detection at different azimuth angles can be achieved by exciting different antenna arrays, so that circumferential recognizing capability of the probe of the nuclear magnetic resonance logging tool can be improved, and the sidewall nuclear magnetic resonance logging tool can be optimized.

Embodiment 4

Embodiment 4 of the present invention provides a probe of a nuclear magnetic resonance logging tool for use in a nuclear magnetic resonance logging-while-drilling tool. In the probe of the nuclear magnetic resonance logging tool provided in this embodiment, the magnet has a cyclic structure, a mud pipe through which drilling fluid is circulated is penetrated through the housing, and the magnet is sleeved on the mud pipe; at least two groups of antenna arrays are uniformly distributed along a circumference of the magnet; each group of the antenna arrays include at least two layers of independently fed antennas, and the first layer antenna is arranged between the magnet and the second layer antenna.

In the probe of the nuclear magnetic resonance logging tool provided in this embodiment, the magnet has a cyclic structure, at least two groups of antenna arrays are distributed at the circumference of the magnet; stratum information detection at different azimuth angles can be achieved by exciting different antenna arrays, so that circumferential recognizing capability of the probe of the nuclear magnetic resonance logging tool can be improved, and the nuclear magnetic resonance logging-while-drilling tool can be optimized.

Embodiment 5

Embodiment 5 of the present invention provides a nuclear magnetic resonance logging tool including the probe of the nuclear magnetic resonance logging tool according to any of the above embodiments. Structures and functions for various components in the probe in this embodiment are similar to those in the above embodiments, and therefore no more details are given herein.

In the nuclear magnetic resonance logging tool provided in the this embodiment, at least two groups of antenna arrays are distributed along a circumference of the magnet, and each group of the antenna arrays include at least two layers of independently fed antennas, stratum information detection at different azimuth angles can be achieved by exciting different antenna arrays, so that circumferential recognizing capability of the probe of the nuclear magnetic resonance logging tool can be improved and three-dimensional (radial, axial and circumferential) stratum detection can be achieved; besides, antennas are arranged in layers outside the magnet, stratum information detection at different radial depths can be achieved by exciting different antennas, and detecting capability at radial depths can be further improved.

Embodiment 6

Embodiment 6 of the present invention provides an antenna excitation method based on the probe of the nuclear magnetic resonance logging tool according to any of the above embodiments. The method in this embodiment includes:

Exciting antennas in one group of antenna arrays, to achieve a mono-azimuth angle detection;

Exciting antennas in at least two groups of antenna arrays, to achieve a multi-azimuth angle detection;

Exciting antennas in different layers of the same antenna array, to achieve detection at different radial depths.

In the antenna excitation method provided in the this embodiment, stratum information detection at different azimuth angles can be achieved by exciting different antenna arrays, so that circumferential recognizing capability of the probe of the nuclear magnetic resonance logging tool can be improved and three-dimensional (radial, axial and circumferential) stratum detection can be achieved; besides, stratum information detection at different radial depths can be achieved by exciting different antennas, and detecting capability at radial depths can be further improved.

Finally, it should be noted that the above embodiments are merely provided for describing the technical solutions of the present invention, but not intended to limit the present invention. It should be understood by persons skilled in the art that although the present invention has been described in detail with reference to the foregoing embodiments, modifications can be made to the technical solutions described in the foregoing embodiments, or equivalent replacements can be made to partial or all technical features in the technical solutions; however, such modifications or replacements do not cause the essence of corresponding technical solutions to depart from the scope of the embodiments of the present invention.

What is claimed is:

1. A probe of a nuclear magnetic resonance logging tool, comprising: a housing, a magnet and an antenna array apparatus; wherein
   the magnet is fixedly arranged in the housing;
   the antenna array apparatus comprises at least two groups of antenna arrays distributed along a circumference of the magnet, and each group of the antenna arrays comprise N layers of independently fed antennas;
   a k-th layer antenna is arranged between the magnet and a (k+1)-th layer antenna, k=1, 2, . . . N−1;
   the antenna is fixed on a support, and the support is fixedly connected to the housing,
   wherein the antenna array apparatus comprises at least one group of reflective antenna arrays, a first layer antenna of the reflective antenna array is a reflective antenna, and a second layer antenna is a saddle-type antenna or a strip-type antenna; and
   the reflective antenna has a greater surface area than the strip-type antenna.

2. The probe of the nuclear magnetic resonance logging tool according to claim 1, wherein the reflective antenna and the strip-type antenna are arc-shaped, a center of the reflective antenna is recessed away from the magnet, and a center of the strip-type antenna is recessed towards the magnet.

3. The probe of the nuclear magnetic resonance logging tool according to claim 2, wherein the strip-type antenna has a less arc curvature than the reflective antenna.

4. The probe of the nuclear magnetic resonance logging tool according to claim 1, further comprising: an antenna excitation circuit for feeding the antenna;
   multiple layers of antennas in the antenna array are electrically connected to the antenna excitation circuit, respectively.

5. The probe of the nuclear magnetic resonance logging tool according to claim 1, wherein, the magnet is a cylindrical magnet, the cylindrical magnet is magnetized radially, and the antenna array apparatus comprises multi groups of antenna arrays uniformly distributed along a circumference of the magnet.

6. The probe of the nuclear magnetic resonance logging tool according to claim 1, wherein, when the nuclear magnetic resonance logging tool is used as a partial tool, the magnet comprises a main magnet and a shielding magnet, both the main magnet and the shielding magnet are of a cuboid shape, and the main magnet has a larger thickness than the shielding magnet;
   the at least two groups of antenna arrays are arranged at one side of the main magnet when the nuclear magnetic resonance logging tool is used as a partial tool.

7. The probe of the nuclear magnetic resonance logging tool according to claim 1, wherein, the magnet has a cyclic structure, a mud pipe through which drilling fluid is circulated is penetrated through the housing, and the magnet is sleeved on the mud pipe;
   the at least two groups of antenna arrays are uniformly distributed along a circumference of the magnet.

8. A nuclear magnetic resonance logging tool comprising the probe of the nuclear magnetic resonance logging tool according to claim 1.

9. An antenna excitation method based on the probe of the nuclear magnetic resonance logging tool according to claim 1, comprising:
   exciting antennas in one group of antenna arrays, to achieve a mono-azimuth angle detection;
   exciting antennas in at least two groups of antenna arrays, to achieve a multi-azimuth angle detection;
   exciting antennas in different layers of the same antenna array, to achieve detection at different radial depths.

* * * * *